US009482656B2

(12) United States Patent
Lee et al.

(10) Patent No.: US 9,482,656 B2
(45) Date of Patent: Nov. 1, 2016

(54) DIAMINE-BASED OIL MARKER COMPOSITIONS AND METHOD OF IDENTIFYING OIL PRODUCT USING THE SAME

(71) Applicants: SK Innovation Co., Ltd., Seoul (KR); SK Energy Co., Ltd., Seoul (KR)

(72) Inventors: Su Jin Lee, Daejeon (KR); Dong Seok Jang, Daejeon (KR); Eun Hee Park, Daejeon (KR); Jin Su Ham, Daejeon (KR); Joon Sik Lee, Daejeon (KR); Jong Ho Lim, Daejeon (KR)

(73) Assignees: SK Innovation Co., Ltd., Seoul (KR); SK Energy Co., Ltd., Seoul (KR)

( * ) Notice: Subject to any disclaimer, the term of this patent is extended or adjusted under 35 U.S.C. 154(b) by 38 days.

(21) Appl. No.: 14/558,094

(22) Filed: Dec. 2, 2014

(65) Prior Publication Data

US 2015/0160183 A1 Jun. 11, 2015

(30) Foreign Application Priority Data

Dec. 5, 2013 (KR) .................. 10-2013-0150339
Nov. 19, 2014 (KR) .................. 10-2014-0161854

(51) Int. Cl.
*C10M 133/00* (2006.01)
*C10L 1/22* (2006.01)
(Continued)

(52) U.S. Cl.
CPC ............... *G01N 33/28* (2013.01); *C10L 1/003* (2013.01); *C10L 1/223* (2013.01); *C10L 1/2222* (2013.01); *C10L 1/232* (2013.01); *C10L 1/233* (2013.01); *C10M 171/007* (2013.01); *G01N 21/78* (2013.01); *C10L 2230/16* (2013.01); *C10M 2215/04* (2013.01); *C10M 2215/06* (2013.01);
(Continued)

(58) Field of Classification Search
CPC ......................... G01N 33/2882; G01N 33/28
USPC .................................... 44/424–434
See application file for complete search history.

(56) References Cited

U.S. PATENT DOCUMENTS 3,719,458 A * 3/1973 Cadorette ............ C10L 1/2222
44/432
4,209,302 A 6/1980 Orelup
(Continued)

FOREIGN PATENT DOCUMENTS

CH 648587 A5 3/1985
DE 4319646 A1 12/1994
(Continued)

OTHER PUBLICATIONS

Popp; "Synthesis of Potential Antineoplastic Agents. XXI. Compounds Related to Ellipticine (1)"; retrieved from URL: http://dfpcorec-p.internal.epo.org/wf/web/citenpl/citenpl.html; Notes; Dec. 1972; pp. 1399-1401.
(Continued)

*Primary Examiner* — Ellen McAvoy
(74) *Attorney, Agent, or Firm* — The Webb Law Firm (57) ABSTRACT

Provided is a method of identifying authenticity of oil by reacting oil marked by a Oil Marker Composition with a developer to develop a color and then measuring absorbance. According to the present invention, an oil maker capable of quantitatively and qualitatively measuring authenticity of oil due to a rapid reaction rate, excellent reproducibility, and distinct color development that may be observed by the naked eyes, and a method of identifying oil using the same.

15 Claims, 3 Drawing Sheets

(51) Int. Cl.

| | | |
|---|---|---|
| *G01N 33/28* | (2006.01) | |
| *C10M 171/00* | (2006.01) | |
| *C10L 1/00* | (2006.01) | |
| *C10L 1/222* | (2006.01) | |
| *C10L 1/223* | (2006.01) | |
| *C10L 1/232* | (2006.01) | |
| *C10L 1/233* | (2006.01) | |
| *G01N 21/78* | (2006.01) | |

(52) U.S. Cl.
CPC .. *C10M 2215/221* (2013.01); *C10M 2215/223* (2013.01); *C10M 2215/225* (2013.01); *C10N 2230/20* (2013.01); *Y10T 436/13* (2015.01)

(56) References Cited

U.S. PATENT DOCUMENTS

| | | | | |
|---|---|---|---|---|
| 4,735,631 A | * | 4/1988 | Orelup | C09B 1/515 |
| | | | | 44/428 |
| 5,205,840 A | * | 4/1993 | Friswell | C10L 1/003 |
| | | | | 44/426 |
| 5,490,872 A | * | 2/1996 | Friswell | C10L 1/003 |
| | | | | 44/328 |
| 5,627,077 A | * | 5/1997 | Dyllick-Brenzinger | C07D 209/08 |
| | | | | 436/106 |
| 5,738,693 A | * | 4/1998 | Dyllick-Brenzinger | C10L 1/003 |
| | | | | 252/401 |
| 5,804,447 A | * | 9/1998 | Albert | C09B 47/045 |
| | | | | 436/172 |
| 6,002,056 A | | 12/1999 | Smith et al. | |
| 8,252,594 B2 | * | 8/2012 | Banavali | C10L 1/003 |
| | | | | 436/139 |
| 8,257,975 B2 | * | 9/2012 | Knapton | C10L 1/003 |
| | | | | 422/420 |
| 2005/0170976 A1 | * | 8/2005 | Lunt | C10L 1/003 |
| | | | | 508/184 |
| 2008/0190354 A1 | * | 8/2008 | Malpas | G01N 21/293 |
| | | | | 116/206 |
| 2015/0160184 A1 | * | 6/2015 | Hanyuda | G01N 31/22 |
| | | | | 436/111 |

FOREIGN PATENT DOCUMENTS

| | | |
|---|---|---|
| GB | 361310 A | 11/1931 |
| KR | 101058120 B1 | 4/2011 |
| WO | 2013050544 A1 | 4/2013 |

OTHER PUBLICATIONS

Harley-Mason et al.; "Isolation and Structure of the Fluorescent Substances Formed in the Oxidative Reaction of Adrenaline and Noradrenaline with Ethylenediamine"; Tetrahedron; 1959; pp. 70-76; vol. 7; Pergamon Press Ltd.

Samejima et al.; "Condensation of Ninhydrin with Aldehydes and Primary Amines to Yield Highly Fluorescent Ternary Products"; Analytical Biochemistry, 1971; pp. 222-236; vol. 42.

Fourche et al.; "Reaction of aliphatic diamines of biological significance with various carbonyl compounds. I. Reaction with ninhydrin."; Bulletin de la Societe de Pharmacie de Bordeaux; 1982; 1 page; vol. 121, nos. 3-4; XP002737732.

Zhou et al.; "Photochemical reaction for synthesis of 1H-benzotriazole and derivatives"; Huaxue Yanjiu Yu Yingyong, 2011; 1 page; vol. 23, No. 12; XP002737733.

Wilson et al.; "Quinoxalinediones. II. The Diels-Alder reactions of 2,3-dimethyl-5,8-quinoxalinedione."; Journal of Organic Chemistry; 1965; 1 page; vol. 30. No. 8; XP002737734.

* cited by examiner

DIAMINE-BASED OIL MARKER COMPOSITIONS AND METHOD OF IDENTIFYING OIL PRODUCT USING THE SAME

CROSS-REFERENCE TO RELATED APPLICATIONS

This application claims priority to Korean Patent Application Nos. 10-2013-0150339 and 10-2014-0161854 filed Dec. 5, 2013 and Nov. 19, 2014, respectively, the disclosures of which are hereby incorporated in their entirety by reference.

TECHNICAL FIELD

The following disclosure relates to a method of identifying authenticity of oil using ninhydrin as a developer.

More particularly, the following disclosure relates to a method of quantitatively and qualitatively identifying authenticity of oil by reacting oil marked by an oil marker composition containing a diamine-based compound with ninhydrin to develop a color.

BACKGROUND

In order to prevent environmental contamination and reducing the lifetime of a vehicle caused by illegal use of petroleum due to the rapid rise in crude oil prices, a petroleum marker for preventing use of adulterated gasoline and illegal use of tax-free oil for a specific purpose has been introduced and used. In addition, as a petroleum purification technology is advanced in accordance with development of a petrochemical technology, each of the oil refinery companies invests large sums of money to ensure and maintain quality competitiveness. Therefore, the oil marker composition has been introduced for brand imaging of each of the oil refinery companies and quality verification. The oil marker composition was firstly added to gasoline, but currently, the oil marker composition is used in up to LPG, diesel, and kerosene.

A marking method for identification of petroleum products has been significantly developed since 1980s, and currently, three types of marking methods have been known.

As the first type, there is i) a method of adding an aromatic material including a diazo group and adding an acid or base to reveal a color, ii) a method of adding an aromatic amine or phenols and then adding diazonium to extract a developer in petroleum (organic solution) and perform qualitative and quantitative analysis, or the like. The above-mentioned methods are cheaply performed and have an excellent color development property, but there are disadvantages in that mechanical measurement is difficult, visual identification should be performed, and it is difficult to carry the developer, etc., such that these methods are not used.

As the second type, there is a method of changing a color of the entire petroleum (organic solution) by injecting a nearly colorless oil marker composition to change a structure of the developer dissolved in petroleum (organic solution). This method is currently mainly used.

As the third type, there is a method of performing mechanical quantitative analysis using a dye absorbing light in near infrared region. However, a used device is significantly expensive and frequently out of order, and solubility of the dye for the petroleum is poor, such that precipitates may be precipitated.

In the first type of identifying authenticity of oil, a method of identifying authenticity of oil using an amine based compound and a derivative thereof may be performed by inducing color development using a quinhydrone reaction, a ninhydrin reaction, a Dragendorff reaction, and the like.

However, in the case of the method of identifying authenticity of oil by reacting the amine based compound and the derivative thereof and ninhydrin as a developer with each other, there were problems in that a reaction rate was significantly slow, heat should be applied in order to induce the reaction, and the reaction was reversible, such that the reaction was not stable, and as a result, reproducibility was low.

RELATED ART DOCUMENT

Patent Document (Patent Document 1) Korean Patent No. 10-1058120
(Patent Document 2) U.S. Patent Publication No. 6002056

SUMMARY

An embodiment of the present invention is directed to providing an oil marker composition containing a diamine-based compound capable of rapidly reacting with ninhydrin at room temperature, and a method of identifying authenticity of oil using the same.

Another embodiment of the present invention is directed to providing a diamine-based oil marker composition capable of causing a distinct change in a color through a ninhydrin reaction in spite of a small content in oil and forming a stable structure to secure high reproducibility, and a method of identifying oil using the same.

In one general aspect, an oil marker composition contains a diamine-based compound represented by the following Chemical Formula (1).

Chemical Formula (1)

(In Chemical Formula (1),
R1 to R4 may be each independently hydrogen, substituted or unsubstituted (C1-C12)alkyl, or (C6-C20)aryl;

A may be (C1-C12)alkylene, (C6-C20)arylene, or (C3-C20)heteroarylene, and the alkylene, arylene, and heteroarylene being each independently substituted with one or more substituents selected from halogen, (C1-C12)alkyl, carboxyl (C=(O)OH), amino, cyano, nitro, and hydroxyl; and the substituent of arylene and heteroarylene of A may be each independently bonded to any one of R1 to R4 to form a ring, the ring being further substituted with one or more substituents selected from halogen, (C1-C12)alkyl, carboxyl (C=(O)OH), amino, cyano, nitro, and hydroxyl.)

In another general aspect, a method of identifying oil includes reacting oil marked by an oil marker composition containing a diamine-based compound represented by the following Chemical Formula (1) with ninhydrin.

Chemical Formula (1)

(In Chemical Formula (1),

R1 to R4 may be each independently hydrogen, substituted or unsubstituted (C1-C12)alkyl, or (C6-C20)aryl;

A may be (C1-C12)alkylene, (C6-C20)arylene, or (C3-C20)heteroarylene, the alkylene, arylene, and heteroarylene being each independently substituted with one or more substituents selected from halogen, (C1-C12)alkyl, carboxyl (C=(O)OH), amino, cyano, nitro, and hydroxyl; and the substituent of arylene and heteroarylene of A may be each independently bonded to any one of R1 to R4 to form a ring, the ring being further substituted with one or more substituents selected from halogen, (C1-C12)alkyl, carboxyl (C=(O)OH), amino, cyano, nitro, and hydroxyl.)

DETAILED DESCRIPTION OF EMBODIMENTS

Hereinafter, the present invention will be described in detail through Examples and drawings, but the Examples are only to describe the gist of the present invention. Meanwhile, the present invention is not limited to process conditions suggested in the following Examples, and it is obvious to those skilled in the art that the process conditions may be optionally selected within a range of conditions required to achieve an object of the present invention.

Here, technical terms and scientific terms used in the present specification have the general meaning understood by those skilled in the art to which the present invention pertains unless otherwise defined, and a description for the known function and configuration unnecessarily obscuring the present invention will be omitted in the following description and the accompanying drawings.

The present invention may provide an oil marker composition containing a diamine-based compound and a method of identifying oil using the same.

More specifically, the present invention may provide a method of qualitatively or quantitatively identifying authenticity of petroleum by reacting oil marked by the oil marker composition containing the diamine-based compound with ninhydrin, which is a developer, to develop a color and observing the color with the naked eyes or measuring absorbance using an absorbance measuring apparatus.

In addition, the present invention may provide a method of identifying oil capable of having excellent reproducibility without a reversible reaction due to a structurally stable product formed by a reaction of the oil marker composition containing the diamine-based compound and ninhydrin and capable of confirming whether or not the color is developed with the naked eyes even with a small amount of the oil marker composition.

That is, the present invention may provide an oil marker composition containing a diamine-based compound represented by the following Chemical Formula (1).

Chemical Formula (1)

(In Chemical Formula (1),

R1 to R4 may be each independently hydrogen, substituted or unsubstituted (C1-C12)alkyl, or (C6-C20)aryl;

A may be (C1-C12)alkylene, (C6-C20)arylene, or (C3-C20)heteroarylene, the alkylene, arylene, and heteroarylene being each independently substituted with one or more substituents selected from halogen, (C1-C12)alkyl, carboxyl (C=(O)OH), amino, cyano, nitro, and hydroxyl; and the substituent of arylene and heteroarylene of A may be each independently bonded to any one of R1 to R4 to form a ring, the ring being further substituted with one or more substituents selected from halogen, (C1-C12)alkyl, carboxyl (C=(O)OH), amino, cyano, nitro, and hydroxyl.)

As used therein, the term [aryl], which is an organic radical derived from an aromatic hydrocarbon by removal of one hydrogen, may mean a monocyclic or polycyclic aromatic hydrocarbon radical and include a form in which two or more aryls are combined through single bond(s). In addition, the aryl may be (C6-C20)aryl, preferably, (C6-C12)aryl.

As an aspect of the present invention, there is provided an oil marker composition containing a diamine-based compound represented by following Chemical Formula (2) or (3).

Chemical Formula (2)

Chemical Formula (3)

(In Chemical Formula (2),

R1 to R4 may be each independently hydrogen, substituted or unsubstituted (C1-C12)alkyl, or (C6-C20)aryl; and n is an integer of 1 to 8.

In Chemical Formula (3),

R1 to R4 may be each independently hydrogen, substituted or unsubstituted (C1-C12)alkyl, or (C6-C20)aryl;

R5 to R8 may be hydrogen, halogen, (C1-C12)alkyl, (C6-C20)aryl, carboxyl (C=(O)OH), amino, cyano, nitro, or hydroxyl;

R5 to R8 may be each independently bonded to each other to form an aromatic ring, a carbon atom of the aromatic ring being further substituted with any one or more hetero atoms selected from N, S, and O; and R1 to R4 may be each independently bonded to any one selected from R5 to R8 to form an aliphatic ring, the aliphatic ring being further substituted with one or more substituents selected from halogen, (C1-C10)alkyl, carboxyl (C=(O)OH), cyano, nitro, and hydroxyl.)

Here, preferably, R1 to R4 may be each independently hydrogen, (C2-C6)alkyl, or (C6-C12)aryl, R5 to R8 may be hydrogen, halogen, (C1-C6)alkyl, (C6-C20)aryl, carboxyl (C=(O)OH), amino, cyano, nitro, or hydroxyl. More preferably, n may be an integer of 1 to 4.

Generally, in the case of normal alkyl amine and a derivative thereof used in order to identify authenticity of oil through a ninhydrin reaction, there were problems in that a reaction rate with ninhydrin corresponding to a developer is significantly slow, and reactivity at room temperature was weak, such that the reaction needs to be induced by heating.

In addition, since a product after reaction was not structurally stable, and accordingly the reaction was reversible, reproducibility was low, such that it was difficult to quantitatively and qualitatively confirm authenticity of oil.

Figure 3:
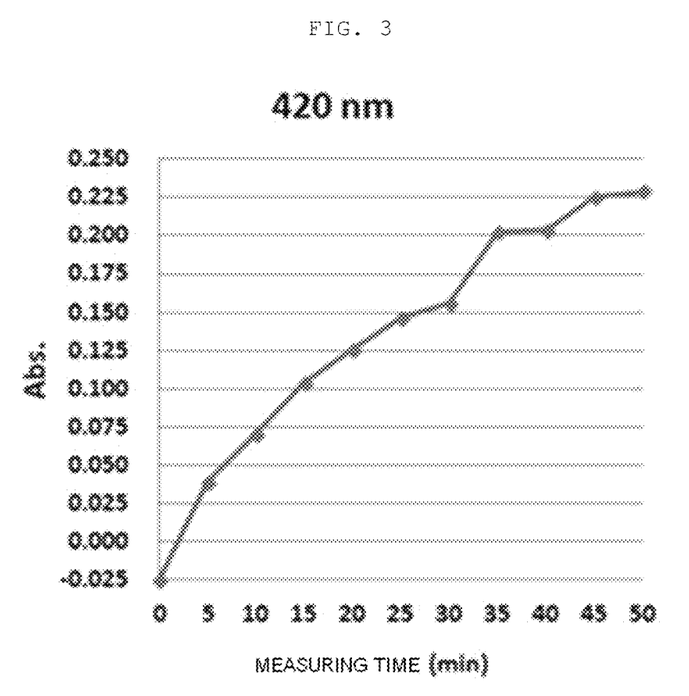
FIG. 3 is an exemplary view showing a change in absorbance of butylamine, which is an example of normal alkyl amine, depending on the time at a wavelength of 420 nm.

In detail, referring to FIG. 3, as shown in a result obtained by measuring absorbance of butylamine, which is an example of normal alkyl amine, depending on time at a wavelength of 420 nm, it may be appreciated that even though a reaction time was over 30 minutes, a reaction was continuously carried out, such that absorbance was increased. Therefore, it may be confirmed that a reaction rate was significantly slow.

Figure 2:
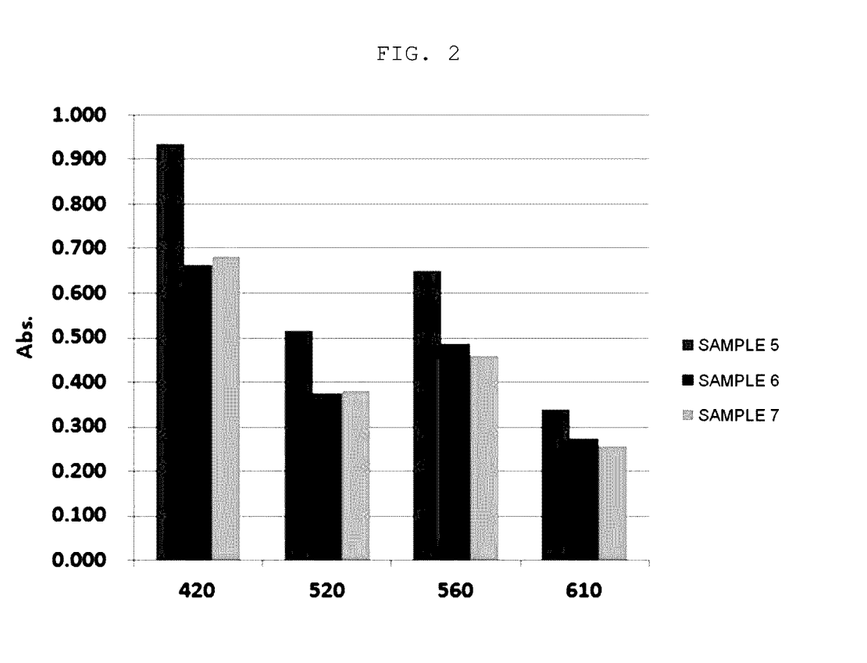
FIG. 2 is an exemplary view showing reproducibility experiment results of butylamine, which is an example of normal alkyl amine, for each sample depending on the wavelength.

In addition, referring to FIG. 2, as a result of measuring absorbance of butylamine, which is the example of normal alkyl amine, in each sample at 420 to 610 nm, the absorbance was significantly different depending on the sample. Therefore, it may be confirmed that a product formed by a reaction of butylamine and ninhydrin was not structurally stable, and the reaction was reversible, such that reproducibility was deteriorated.

Figure 1:
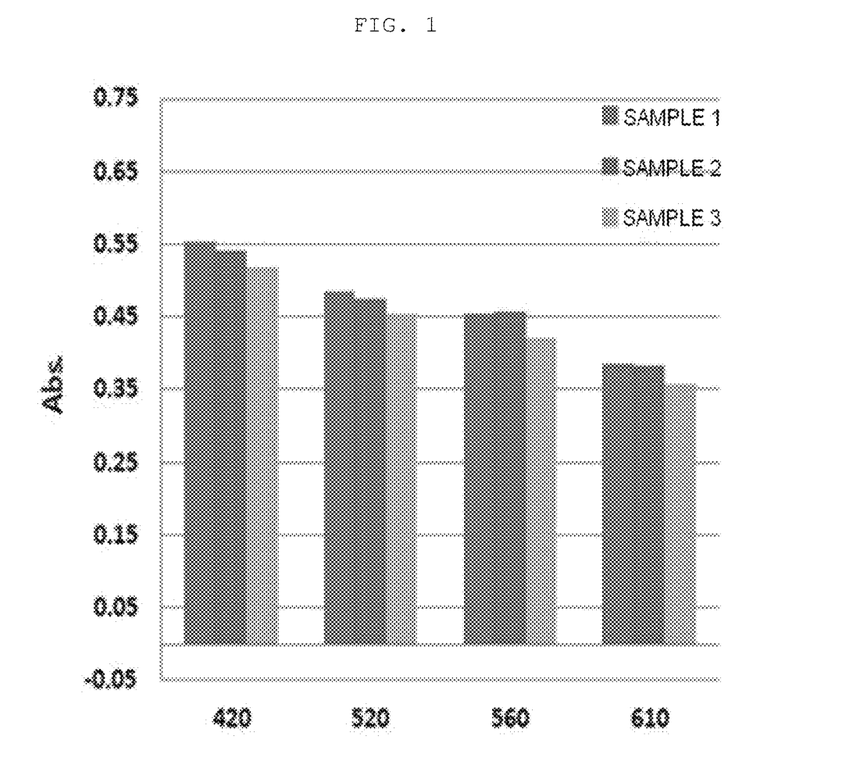
FIG. 1 is an exemplary view showing reproducibility experiment results of ethylenediamine, which is an example of an oil marker composition containing a diamine-based compound according to the present invention, for each sample.

However, as shown in a result of measuring reproducibility of ethylenediamine, which is an example of a diamine-based oil marker composition according to the present invention, depending on the wavelength of FIG. 1, the oil marker composition containing the diamine-based compound represented by Chemical Formula (2) or (3) according to the present invention may rapidly react with ninhydrin at room temperature and be structurally stable to thereby have excellent reproducibility. In addition, even though a small amount of the oil marker composition according to the present invention is contained in oil, the oil marker composition may induce a color development reaction with ninhydrin.

As the oil marker composition containing the diamine-based compound according to the present invention, any material may be used without limitation as long as in Chemical Formula (2), R1 to R4 are each independently hydrogen, substituted or unsubstituted (C1-C12)alkyl, more preferably, (C2-C6)alkyl, or (C6-C20)aryl, and n is an integer of 1 to 8, preferably 1 to 4. As an example of the oil marker composition, there is ethylenediamine, trimethylenediamine, 1,5-diamino-2-methylpentane, 1,3-diaminopropane, 1,4-diaminobutane, or the like, but the present invention is not limited thereto.

As the oil marker composition containing the diamine-based compound according to the present invention, any material may be used without limitation as long as in Chemical Formula (3), R1 to R4 are each independently hydrogen, substituted or unsubstituted (C1-C12)alkyl, more preferably, (C2-C6)alkyl, or (C6-C20)aryl, R5 to R8 are hydrogen, substituted or unsubstituted (C1-C12)alkyl (which are the same as or different from each other), more preferably, (C1-C6)alkyl or (C6-C20)aryl. As an example of the oil marker composition, there is ortho-phenylenediamine, 1,2-diamino-3,5-dimethylbenzene, or the like, but the present invention is not limited thereto.

In addition, R5 and R6, R6 and R7, or R7 and R8 in Chemical Formula (3) may be bonded to each other and may form an aromatic ring including C or N.

That is, in the diamine-based oil marker composition according to the present invention, R5 and R6, R6 and R7, or R7 and R8 in Chemical Formula (3) may be bonded to each other to thereby form the aromatic ring including C or N.

As used herein, the term [aromatic ring], which includes (C6-C50)aryl or (C6-C50)heteroaryl, may mean a monocyclic or polycyclic ring, and the heteroaryl may include at least one hetero atom selected from O, N, S, Si, and P. The aromatic ring may be preferably a (C6-C30) aromatic ring, more preferably, a (C6-C20) aromatic ring, but is not limited thereto.

A representative example of a compound of Chemical Formula (3) in which R5 and R6, R6 and R7, or R7 and R8 are bonded to each other to thereby form an aryl group including C or N may include compounds represented by the following Chemical Formulas (4) to (6), but is not limited thereto.

Chemical Formula (4)

Chemical Formula (5)

Chemical Formula (6)

Further, in the compound of Chemical Formula (3) according to the present invention, R1 or R2 may be bonded to R8, and R3 or R4 may be bonded to R5, thereby forming an aliphatic ring.

More specifically, in Chemical (3), R1 or R2 may be bonded to R8, and R3 or R4 may be bonded to R5, thereby forming a 5-membered or 6-membered aliphatic ring.

As used herein, the term [aliphatic ring], which includes (C6-C50)cycloalkyl or (C6-C50)heterocycloalkyl, may mean a monocyclic or polycyclic ring, and the heterocycloalkyl may include at least one hetero atom selected from O, N, S, Si, and P. The aliphatic ring may be preferably a (C6-C30) aliphatic ring, more preferably, a (C6-C20) aliphatic ring, but is not limited thereto.

Here, preferably, the heterocycloalkyl may include a nitrogen atom, an oxygen atom, a sulfur atom, or the like, in addition to a carbon atom.

An example of the oil marker composition containing the diamine-based compound represented by Chemical Formula (3) including the aliphatic ring may include compounds represented by the following Chemical Formulas (7) to (10), or the like, but is not limited thereto.

Chemical Formula (7)

Chemical Formula (8)

Chemical Formula (9)

Chemical Formula (10)

Here, R9 to R11 may be hydrogen, substituted or unsubstituted (C1-C12)alkyl (which are the same as or different from each other), more preferably (C1-C6)alkyl, or (C6-C20)aryl.

In addition, the present invention relates to a method of identifying authenticity of oil by reacting oil marked by the oil marker composition containing the diamine-based compound represented by the following Chemical Formula (1) with ninhydrin to induce color development.

That is, the present invention relates a method of identifying oil including reacting oil marked by an oil marker composition containing a diamine-based compound represented by the following Chemical Formula (1) with ninhydrin.

In the method of identifying oil according to the present invention, as compared to a method of identifying oil using normal alkyl amine and a derivative thereof as an oil marker composition, a rapid reaction rate may be secured even at room temperature and authenticity of oil may be identified with excellent reproducibility by using a structurally stable oil marker composition.

The oil marker composition used in the method of identifying oil according to the present invention may include all of the above-mentioned diamine based compounds according to the present invention.

According to the present invention, a content of the oil marker composition containing the diamine-based compound represented by Chemical Formula (1) in the oil is not limited, but may be preferably 1 ppm or more. There is no limitation in the maximum content of the oil marker composition, but it is more preferable that the oil marker composition is used in a range of 1 to 500 ppm. However, the present invention is not limited thereto.

That is, even though only a small amount of the oil marker composition containing the diamine-based compound represented by Chemical Formula (1) is contained in oil, the oil marker composition may generate a color reaction by ninhydrin and induce color development enough to identify authenticity of oil with the naked eyes.

A developer reacting with the oil containing the oil marker composition containing the diamine-based compound represented by Chemical Formula (1) is ninhydrin and may be represented by the following Chemical Formula (11).

Chemical Formula (11)

A concentration of the ninhydrin developer reacting with the oil marker composition according to the present invention is not particularly limited and may be various, but it is preferable that the ninhydrin developer is contained in an enough amount to react with a diamine-based marker contained in a sample collected from petroleum products containing the oil marker composition to thereby develop a color.

As a non-restrictive example, an amount of the ninhydrin developer may be 1 ppm or more and there is no limitation in the maximum amount, but the amount of the ninhydrin developer may be preferably 1 to 10,000 ppm, more preferably 1 to 5,000 ppm. However, the present invention is not limited thereto.

In the case of inducing the ninhydrin reaction of the ninhydrin developer as described above and the oil marker composition containing the diamine-based compound represented by Chemical Formula (1), whether or not a color is developed may be confirmed with the naked eyes, and the developed color may be dark yellow or purple, but is not limited thereto.

That is, in the case in which the oil marked by the oil marker composition containing the diamine-based compound represented by Chemical Formula (1) according to the present invention reacts with ninhydrin, which is the developer, color development occurs in the oil, and the color development may be qualitatively identified by the naked eyes. Further, in the case of using an absorbance measuring apparatus, the color development may be quantitatively measured.

Therefore, the method of identifying oil according to the present invention may be a method of identifying oil including: reacting oil marked by an oil marker composition containing the diamine-based compound represented by Chemical Formula (1) with ninhydrin; and measuring absorbance using an absorbance measuring apparatus.

Any absorbance measuring apparatus may be used without limitation as long as color development may be quantitatively measured, but considering that authenticity of oil may be instantly identified in the field, a portable UV/Vis spectrophotometer is preferable, but the present invention is not limited thereto.

As oil that may be identified by the method of identifying oil according to the present invention, any oil may be used as long as it may dissolve the diamine-based compound represented by Chemical Formula (1) as the oil marker composition. A non-restrictive example of the oil may include mineral oil, base oil, kerosene, lubricating oil, gasoline, mixed oil thereof, or the like, but is not limited thereto.

Hereinafter, Preparation Examples of the oil marker composition containing the diamine-based compound according to the present invention and Examples of reacting oil marked by the oil marker composition with ninhydrin and measuring absorbance will be described, but it is obvious to those skilled in the art that the following Examples are only examples according to the present invention and do not limit the technical idea of the present invention.

Preparation Example 1

Preparation of Disulfonamide

Ortho-phenylenediamine (4.1 g) was dissolved in dichloromethane (100 mL) and then cooled to 0° C. Pyridine (6.1 mL) and para-toluenesulfonyl chloride (14.5 g) were slowly injected into the solvent and then heated to room temperature (23° C.), followed by stirring for 1 hour. A reaction was terminated by injecting water, and the produced solid was obtained by filtration. The solid product was washed with water again and dried under reduced pressure, thereby obtaining disulfonamide (10.8 g) as a white solid. A structure of the prepared material was confirmed by nuclear magnetic resonance (NMR) analysis: $^1$H NMR (500 MHz, CDCl$_3$) δ 7.57 (4H, d, J=8.0 Hz), 7.22 (4H, d, J=8.0 Hz), 7.06-6.99 (2H, m), 6.98-6.91 (2H, m), 6.88 (2H, s), 2.39 (6H, s)

Preparation Example 2

Preparation of Dimethyl Disulfonamide

Sodium hydride (60%, 1.2 g) dispersed in mineral oil was cooled to 0° C. and slowly injected into N,N-dimethylformamide (20 mL) being stirred. Disulfonamide (4.2 g) prepared in Preparation Example 1 was injected thereinto and then stirred at 0° C. for 15 minutes. Iodomethane (5 mL) was slowly injected thereinto, heated to room temperature, and stirred for 6 hours. A reaction was terminated by injecting water, and the produced solid was obtained by filtration. The solid product was washed with water again and dried under reduced pressure, thereby obtaining dimethyl disulfonamide (4.5 g) as a white solid. A structure of the prepared material was confirmed by nuclear magnetic resonance (NMR) analysis: $^1$H NMR (500 MHz, CDCl$_3$) δ 7.72 (4H, d, J=8.0 Hz), 7.33 (4H, d, J=8.0 Hz), 7.29-7.20 (2H, m), 6.94-6.84 (2H, m), 3.21 (6H, s), 2.48 (6H, s)

Preparation Example 3

Preparation of N,N'-Dimethyl Ortho-Phenylenediamine (Oil Marker Composition According to the Present Invention)

Dimethyl disulfonamide (4.5 g) prepared in Preparation Example 2 was dissolved in 90% sulfuric acid (28 mL) and heated to 100° C., followed by stirring 8 hours. After cooling the resultant to room temperature, ice was injected thereto and solid sodium hydroxide was slowly injected thereto to adjust pH to 11. After stirring the mixture for 1 hour, the mixture was extracted with diethylether (100 mL). After the extracted organic layer was dried by injecting sodium sulfate, followed by distillation under reduced pressure, thereby obtaining N,N'-dimethyl ortho-phenylenediamine (1.9 g) as a colorless liquid. A structure of the prepared material was confirmed by nuclear magnetic resonance (NMR) analysis: $^1$H NMR (500 MHz, CDCl$_3$) δ 6.86-6.80 (2H, m), 6.71-6.64 (2H, m), 3.27 (2H, br s), 2.86 (6H, s)

Example 1

10 mg of ethylenediamine was added to 1 kg of kerosene. In the case of putting 10 mL of the prepared solution into a 20 mL glass bottle and then adding 0.2 mL of a ninhydrin indicator thereto as a developer, a solution color was changed to purple. In this case, when absorbance was measured using a spectrometer, the maximum absorbance was obtained at 420 nm.

Example 2

10 mg of 1,4-aminobutane was added to 1 kg of kerosene. In the case of putting 10 mL of the prepared solution into a 20 mL glass bottle and then adding 0.2 mL of a ninhydrin indicator thereto as a developer, a solution color was changed to purple. In this case, when absorbance was measured using a spectrometer, the maximum absorbance was obtained at 420 nm.

Example 3

10 mg of ortho-phenylenediamine was added to 1 kg of kerosene. In the case of putting 10 mL of the prepared solution into a 20 mL glass bottle and then adding 0.2 mL of a ninhydrin indicator thereto as a developer, a solution color was changed to yellow. In this case, when absorbance was measured using a spectrometer, the maximum absorbance was obtained at 520 nm.

Example 4

10 mg of 2.3-diaminonaphthalene was added to 1 kg of kerosene. In the case of putting 10 mL of the prepared solution into a 20 mL glass bottle and then adding 0.2 mL of a ninhydrin indicator thereto as a developer, a solution color was changed to yellow. In this case, when absorbance was measured using a spectrometer, the maximum absorbance was obtained at 520 nm.

Example 5

10 mg of N,N'-dimethyl ortho-phenylenediamine was added to 1 kg of kerosene. In the case of putting 10 mL of the prepared solution into a 20 mL glass bottle and then adding 0.2 mL of a ninhydrin indicator thereto as a developer, a solution color was changed to yellow. In this case, when absorbance was measured using a spectrometer, the maximum absorbance was obtained at 520 nm.

Example 6

10 mg of 2,3-diaminophenazine was added to 1 kg of kerosene. In the case of putting 10 mL of the prepared solution into a 20 mL glass bottle and then adding 0.2 mL of a ninhydrin indicator thereto as a developer, a solution color was changed to yellow. In this case, when absorbance was measured using a spectrometer, the maximum absorbance was obtained at 520 nm.

Example 7

10 mg of 8-amino-1,2,3,4-tetrahydroquinoline was added to 1 kg of kerosene. In the case of putting 10 mL of the prepared solution into a 20 mL glass bottle and then adding 0.2 mL of a ninhydrin indicator thereto as a developer, a solution color was changed to yellow. In this case, when absorbance was measured using a spectrometer, the maximum absorbance was obtained at 520 nm.

there are advantages such as excellent reactivity even at room temperature and a short reaction time, as compared to normal alkyl amine.

The oil marker composition containing the diamine-based compound according to the present invention may rapidly react with ninhydrin at room temperature (23° C.) to develop a color, thereby making it possible to quantitatively and qualitatively measure authenticity of oil.

Further, since the product formed by the reaction between the oil marker composition containing the diamine-based compound according to the present invention contained in the oil and ninhydrin may have excellent stability, distinctly change the color, and have excellent reproducibility, even

TABLE 1

Comparison of Absorbance and Reaction Time between Oil Marker Composition containing the Diamine-Based Compound According to Present Invention and Normal Alkyl Amine Compound

| | Chemical Formula of Compound | Reaction Temperature | Maximum Absorbance | Reaction Time |
|---|---|---|---|---|
| Example 1 |  | Room Temperature | 420 nm | within 30 seconds |
| Example 2 |  | Room Temperature | 420 nm | within 30 seconds |
| Example 3 |  | Room Temperature | 520 nm | within 30 seconds |
| Example 4 |  | Room Temperature | 520 nm | within 30 seconds |
| Example 5 |  | Room Temperature | 520 nm | within 30 seconds |
| Example 6 |  | Room Temperature | 520 nm | within 30 seconds |
| Example 7 |  | Room Temperature | 520 nm | within 30 seconds |
| Comparative Example |  | Room Temperature | 420 nm | Reaction continuously proceeds for 5 minutes or more |

As described above, in the case of reacting the oil marked by the diamine-based Oil Marker Composition according to the present invention with ninhydrin used as a developer, though only a small amount of the oil marker composition is contained in the oil, the oil marker composition may induce color development.

What is claimed is:

1. An oil marker composition comprising a diamine-based compound represented by the following Chemical Formulae (2) or (3), and generating a color reaction by ninhydrin:

Chemical Formula (2)

Chemical Formula (3)

(In Chemical Formula (2),

R1 to R4 are each independently substituted or unsubstituted (C1-C12)alkyl, or hydrogen;

n is an integer of 1 to 8, and in Chemical Formula (3),

R1 to R4 are each independently hydrogen, substituted or unsubstituted (C1-C12)alkyl, or (C6-C20)aryl;

R5 to R8 are each independently hydrogen, halogen, (C1-C12)alkyl, (C6-C20)aryl, carboxyl (C=(O)OH), amino, cyano, nitro, or hydroxyl;

R5 to R8 are each independently bonded to each other to form an aromatic ring, a carbon atom of the aromatic ring being substituted with any one or more hetero atoms selected from N, S, and O; and

R1 to R4 are each independently bonded to any one selected from R5 to R8 to form an aliphatic ring, the aliphatic ring being further substituted with one or more substituents selected from halogen, (C1-C10)alkyl, carboxyl (C=(O)OH), cyano, nitro, and hydroxyl).

2. The oil marker composition of claim 1, wherein in Chemical Formula (3), R5 and R6, R6 and R7, or R7 and R8 are bonded to each other to form an aromatic ring including C or N.

3. The oil marker composition of claim 2, wherein the diamine-based compound of Chemical Formula (3) in which the aromatic ring including C or N is formed is any one selected from compounds represented by the following Chemical Formulas (4) to (6)

Chemical Formula (4)

Chemical Formula (5)

Chemical Formula (6)

4. The oil marker composition of claim 1, wherein in Chemical Formula (3), R1 or R2 is bonded to R8, and R3 or R4 is bonded to R5, thereby forming a 5-membered or 6-membered aliphatic ring.

5. The oil marker composition of claim 4, wherein a diamine-based compound of Chemical Formula (3) in which the 5-membered or 6-membered aliphatic ring is formed is any one selected from compounds represented by Chemical Formulas (7) to (10)

Chemical Formula (7)

Chemical Formula (8)

Chemical Formula (9)

Chemical Formula (10)

(in Chemical Formulas (7) to (10),

R9 to R11 are hydrogen, substituted or unsubstituted (C1-C12)alkyl (which are the same as or different from each other), or (C6-C20)aryl).

6. A method of identifying oil comprising: reacting oil marked by the oil marker composition containing the diamine-based compound represented by Chemical Formula (3) of claim 1, with ninhydrin.

7. The method of identifying oil of claim 6, wherein in Chemical Formula (3), R5 and R6, R6 and R7, or R7 and R8 are bonded to each other to form an aromatic ring including C or N.

8. The method of identifying oil of claim 7, wherein the diamine-based compound of Chemical Formula (3) in which the aromatic ring including C or N is formed is any one selected from the compounds represented by the following Chemical Formulas (4) to (6) of claim 3.

9. The method of identifying oil of claim 8, wherein in Chemical Formula (3), R1 or R2 is bonded to R8, and R3 or R4 is bonded to R5, thereby forming a 5-membered or 6-membered aliphatic ring.

10. The method of identifying oil of claim 9, wherein a diamine-based compound of Chemical Formula (3) in which the 5-membered or 6-membered aliphatic ring is formed is any one selected from the compounds represented by Chemical Formulas (7) to (10) of claim 5.

11. The method of identifying oil of claim 6, further comprising measuring absorbance using an absorbance measuring apparatus.

12. The method of identifying oil of claim 11, wherein a diamine-based compound represented by Chemical Formulae (2) or (3) is contained at a content of 1 to 500 ppm in the oil.

13. The method of identifying oil of claim 12, wherein the oil is any one selected from mineral oil, base oil, kerosene, lubricating oil, and gasoline.

14. The method of identifying oil of claim 13, wherein absorbance measured using the absorbance measuring apparatus is 400 to 800 nm.

15. The method of identifying oil of claim 14, wherein the absorbance measuring apparatus is a portable UV/Vis spectrophotometer.

\* \* \* \* \*